United States Patent
Midgely

[11] Patent Number: 5,962,339
[45] Date of Patent: Oct. 5, 1999

[54] ANALYTICAL DEVICE FOR DETERMINING THE PRESENCE OF AN ANALYTE IN A LIQUID SAMPLE ABOVE A PREDETERMINED VALUE

[75] Inventor: John S. Midgely, Ilkley, United Kingdom

[73] Assignee: Tepnel Medical Limited, Knutsford, Chesire, United Kingdom

[21] Appl. No.: 08/886,322

[22] Filed: Jul. 1, 1997

[51] Int. Cl.$^6$ .................................................. G01N 33/546
[52] U.S. Cl. ............................ 436/534; 436/518; 436/525; 436/531; 436/810; 435/5; 435/7.1; 435/970; 422/56
[58] Field of Search ................................ 435/5, 7.1, 7.92, 435/7.93, 970; 436/514, 518, 525, 531, 810, 534; 422/56

[56] References Cited

U.S. PATENT DOCUMENTS

| | | | |
|---|---|---|---|
| 5,541,069 | 7/1996 | Mortensen et al. | 435/7.9 |
| 5,585,241 | 12/1996 | Lindmo | 435/6 |
| 5,780,308 | 7/1998 | Ching et al. | 436/514 |

FOREIGN PATENT DOCUMENTS

| | | |
|---|---|---|
| WO 91/19980 | 12/1991 | WIPO . |
| WO 92/22797 | 12/1992 | WIPO . |
| WO 93/03175 | 2/1993 | WIPO . |
| WO 93/15230 | 8/1993 | WIPO . |

*Primary Examiner*—Jeffrey Stucker
*Attorney, Agent, or Firm*—Woodard, Emhardt, Naughton, Moriarty & McNett

[57] ABSTRACT

An analytical device for use in determining the presence of an analyte species of interest in a liquid state includes a chromatographic membrane support along which the liquid may travel, a plurality of first detectable particles associated with a sampling region of the device at which the liquid is to be applied, the particles being capable of being moved along the support by the liquid travel and having immobilised thereon a first binding agent capable of forming a first complex with the analyte species, a threshold region provided downstream of the sampling region in the direction of liquid travel, the threshold region being provided with a second binding agent which is capable of binding to non-complexed first binding agent on the particles, and which is present in an amount, such that a detectable number of the particles only pass the threshold region if the amount of analyte species in the sample is above a predetermined level, and a detection region downstream of the threshold region in the direction of liquid travel, the detection region comprising a third binding agent capable of binding to the first complex on the particles.

21 Claims, 1 Drawing Sheet

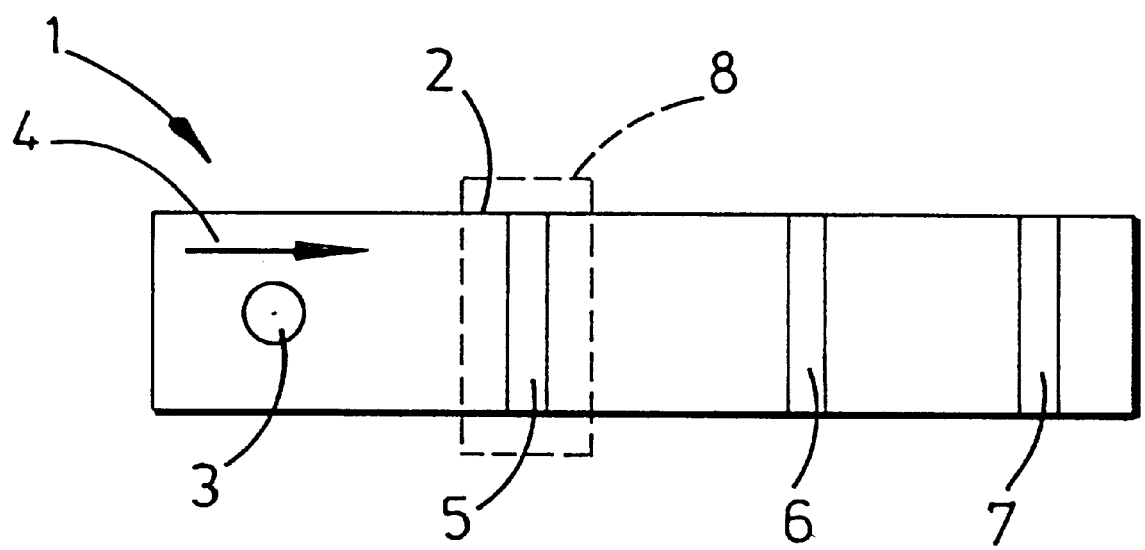

ANALYTICAL DEVICE FOR DETERMINING THE PRESENCE OF AN ANALYTE IN A LIQUID SAMPLE ABOVE A PREDETERMINED VALUE

The present invention relates to an analytical device for use in the detection of a component of interest in a liquid sample.

U.S. Pat. No. 5,238,652 (Drug Screening Systems, Inc.) discloses an analytical device based on an immunochromotragraphic technique for use in the detection of non-protein antigens in a liquid sample, e.g. a drug metabolite in urine. The device is intended for use by non-skilled personnel and comprises a chromatographic membrane support having a plurality of first, coloured latex beads which are sensitised with antibodies for the antigen being detected.

Upon application of liquid to the support, the liquid moves along the support and carries with it the latex beads.

Downstream of the point at which the liquid is applied, there is provided an immobilised drug conjugate probe which is capable of binding to antibodies on the latex particle. The drug conjugate probe is immobilised on the membrane and is arranged in a band transverse to the direction of liquid movement.

In a preferred embodiment, the device further comprises second, coloured latex particles provided at the same location as the first particles. The second particles are provided with immobilised immunoreaction protein antibodies which will not bind to the drug conjugate probe on the support but which will bind to an immobilised inimunoreaction antibody probe (again provided in a band) downstream of the immobilised drug conjugate probe.

In use of the device, the liquid sample is applied to the support in the region of the latex beads and the movement of the liquid carries the beads along the support to the first band (i.e. the inmmobilised drug conjugate probe). If antigen is not present in the sample, then the antibodies on the first beads react with the immobilised drug conjugate probe and become immobilised on the support thereby forming a coloured band. Conversely, if antigen is present in the sample, all of the antibodies on the first beads bind to the antigen and cannot therefore bind to the immobilised drug conjugate probe. In either case, the second particles move past the drug conjugate probe until they reach the immobilised immunoreaction antibody with which they will bind. Therefore a coloured band is formed at the region of the immobilised immunoreaction antibody. This is a control band which indicates that the device is operative.

Therefore, assuming that the antigen was present in the test sample, there will be one coloured band on the support, i.e. at the location of the immobilised immunoreaction antibody. In the case of a negative result, there will be two coloured bands.

We consider it to be a disadvantage of the device that a negative result gives rise to two bands whereas a positive result gives rise only to a single band (and in fact no band at all if latex particles including the "control" immunoreaction protein antibodies are not present). Normal experience would suggest that a positive result for the test would give more coloured bands than a negative result. There is thus the danger that the result of the test could be misinterpreted, i.e. a negative result is taken as positive or vice versa.

It is therefore an object of the present invention to provide an analytical device in which the abovementioned disadvantages are obviated or mitigated.

According to the present invention there is provided an analytical device for use in determining the presence of analyte species of interest in a liquid sample, the device comprising a chromatographic membrane support along which the liquid may travel, a plurality of first detectable particles associated with a sampling region of the device at which liquid is to be applied, said particles being capable of being moved along the support by said liquid travel and having immobilised thereon a first binding agent capable of forming a first complex with said analyte species, a threshold region provided downstream of the sampling region in the direction of liquid travel, said threshold region being provided with a second binding agent which is capable of binding to species on the particles, and which is present in an amount, such that a detectable number of said particles only pass the threshold region if the amount of the analyte species in the sample is above a predetermined level, and a detection region downstream of said threshold region in the direction of liquid travel, said detection region comprising a third binding agent capable of binding to the first complex on the particles.

In use of the device according to the invention, the liquid sample potentially containing the analyte species of interest is applied to the sampling region. As a result, the liquid is caused to travel along the chromatographic membrane support and the beads are carried along with the liquid. Prior to the beads reaching the threshold region, the analyte species of interest (if present) in the liquid sample will have reacted with the first binding agent present on the particles.

At the threshold region, there is a second binding agent. The nature and amount of this binding agent is such that detectable quantities of the particles are only carried (by the liquid travel) downstream of the threshold region if the amount of the analyte species is above a predetermined level Particles which pass the threshold region reach the detection region where they are immobilised by virtue of the presence of the third binding agent.

Therefore if the liquid sample contains more than a predetermined amount of the analyte species, then detectable quantities of the particles pass to and are retained at, the detection region. If particles are detected at the detection region then the result of the test is positive.

Conversely, if the liquid sample does not contain any of the analyte species of interest, or only contains this species below a predetermined amount, then detectable amounts of the particles do not pass to the detection region. The absence of detectable quantities of the particles at the detection region can therefore be taken as a "negative result" in that the sample either did not contain the analyte species or did so in an amount below a predetermined level.

The sampling region may also contain a set of second detectable particles which have immobilised thereon an immunological component which will not bind to the analyte species, the first binding agent, the second binding agent nor the third binding agent but which will nevertheless bind to a complementary immunological component provided downstream of the detection region. During a test, these second particles will pass through both the threshold and detection regions but will become immobilised at the control region at which they may be detected. These particles provide a control to demonstrate that the device is working effectively. The immunological component provided on the second particles may, for example, be BSA and the complementary immunological component provided at the control region may be an antibody therefor (e.g. Sheep anti BSA).

It will be appreciated from the foregoing description that an important feature of the device of the invention is the threshold region. As explained, this region is such that detectable quantities of the particles only pass this region if analyte is present in the sample, or at least present in a minimum, predetermined amount The factors which influence whether or not detectable quantities of particles will pass the threshold region are as follows:

(a) the amount of analyte species (if any) in the sample;

(b) the type and number of particles;

(c) the amount of first binding agent immobilised on the particles;

(d) the amount of second binding agent;

(e) the type of membrane support and the distance between the sampling region and the threshold region.

Assume that for a given device, the features (b), (c) and (e) are constant. It is possible to determine empirically the amount of second binding agent which is required to allow detectable quantities of the particles to pass the threshold region for any given minimum amount of analyte species in the sample.

It will thus be appreciated that the device may readily be tailored to allow detectable quantities of the particles to pass to the detection region for any given minimum quantity of the analyte species. In the simplest embodiment of the invention, the device is constructed so as simply to indicate whether or not there is a certain minimum quantity of the analyte species in the sample. Thus if particles are detected at the detection region the analyte was present in more than a predetermined minimum amount. This embodiment does not provide any further information as to the amount of analyte in the sample.

In a development of the invention, the detection region may comprise a number of bands of the third binding agent transverse to the path of analyte travel each of which allows a detectable quantity of particles to pass to the next band if the amount of analyte species is above a predetermined level. Explained alternatively, detection of particles at the first 'detection band' would show that the sample continued an amount of at least, say, x of the analyte species. Detection of particles at the second 'detection' band would show that the sample contained an amount of at least, say, y of the analyte species where y>x and similarly for the third and successive 'detection bands'.

The amount of third binding agent required to be present in each such detection band may be determined empirically.

It is preferred that the device functions on the basis of an immunoassay technique. Therefore the analyte may be an antibody or antigen and the first binding agent is an immunological complement thereof.

By way of example, if the analyte species to be determined is an antibody, the device may comprise the following components:

| | |
|---|---|
| First Binding Agent (Immobilised on Beads) | Antigen to Analyte Antibody |
| Second Binding Agent (Immobilised at Threshold Region) | Antibody, Receptor or Selective Binding Agent |
| Third Binding Agent (Immobilised at Detection Region) | Antibody to Complex formed between Analyte Antibody and First Binding Agent |

The first binding agent may for example be a hapten such as a protein or protein derivative, or a nucleic acid.

In use of the device, the analyte antibody reacts with the first binding agent on the particles. If the amount of analyte antibody is in excess compared to the amount of first binding agent then all of the latter will be complexed and (before the particles reach the threshold region) therefore not available for binding with the second binding agent. As such, all of the particles will pass through the threshold region.

If however the analyte antibody is not in excess but nevertheless present in the sample above a predetermined amount, a detectable amount of particles may still pass beyond the threshold region. Whilst we do not wish to be bound by any particular theory, we believe that a proportion (as governed by a statistical distribution) of the particles have their antigen fully complexed with the analyte antibody and it is these particles which pass the threshold region.

An alternative construction of device for use in determining the presence of an antigen in a sample comprises the following components

| | |
|---|---|
| First Binding Agent (Immobilised on Beads) | Antibody or Selective Binding Agent for complexing with analyte antigen |
| Second Binding Agent (Immobilised at Threshold Region) | Antigen capable of complexing with First Binding Agent |
| Third Binding Agent | Antibody to Complex formed between Analyte Antigen and First Binding Agent |

Conveniently, the particles are of a contrasting colour to the membrane support. As such, the presence or otherwise of detectable quantities of particles may be determined by visual inspection of the region. A coloration (relative to the background colour of the membrane) at this region corresponds to a positive result and no coloration indicates a negative result. If the particles are to be detected visually then it is preferred that the threshold region is obscured from view (possibly selectively) since a similar coloration to that which could be produced at the detection region is also be produced at the threshold region. Obscuring the threshold region from view prevents misinterpretation of the results of the test.

Alternatively the particles may be fluorescent and this may be advantageous for increasing the sensitivity of the device.

The particles conveniently have a size in the range 1–5 microns. For preference, the particles are of latex. Coloured latex beads are particularly preferred.

The support should be a homogenous continuous matrix. Which allows even fluid flow. The membrane may for example be of nylon or nitrocellulose.

In order to function effectively, the device is arranged so that the distance which the liquid travels before reaching the threshold region, and the rate at which the liquid travels along the support, are such that there is sufficient time for the analyte species (if present) to react with the immobilised first binding agent (on the particles) before the threshold region is reached. Furthermore, the rate of travel of the liquid through the threshold region should not be so high that particles are not retained within the threshold region nor too low such that all particles are retained in the region, irrespective of whether or not the first complex has been formed on the particles. These parameters (i.e. the values for (i) the distance between point of liquid application and the threshold region and (ii) rate of travel of the liquid) may be determined empirically by standard techniques.

The device is preferably provided with a controlled release means to which the liquid sample is applied and from which the liquid passes onto the membrane at an appropriate rate. Examples of suitable controlled release means are a filter pad or a sponge. It is preferred that the particles are provided within the controlled release means.

The advice of the invention may be used for a variety of analytes including antigens, antibodies, haptens, DNA, RNA, a cell, or a virus.

The device is particularly useful for detecting drug metabolites in urine but may be used for the detection of other types of antigen in either urine or other liquid samples.

The invention will be further described by way of example only with reference to the accompanying drawing which schematically illustrates (in plan view) one embodiment of analytical device in accordance with the invention.

The illustrated device 1 is intended for use in determining as to whether or not a particular hapten H is present in a liquid sample, e.g. urine. The hapten may for example be a drug or metabolite, the test being conducted to see whether a person has taken the particular drug which gives rise to the hapten as a metabolite.

The device 1 comprises an elongate chromatographic membrane 2 along which liquid will flow by capillary action and onto which is mounted (towards one end thereof) a sponge 3 providing a controlled release means. The arrangement is such that liquid sample applied to the sponge 3 will be released onto the membrane 2 and flow in the direction of arrow 4.

On the membrane 2 are three binding regions which going in the direction of arrow 4, are successively referenced as 5, 6 and 7 as depicted in the drawing. The function of these regions will be described below.

Provided within the sponge 3 are two sets of coloured latex beads (not shown) having sizes in the range of 1 to 20 microns. One set of beads has immobilised thereon an antibody Ab for the hapten H to be tested. The other set of beads has Bovine Serum Albumin (BSA) immobilised thereon. The antibody Ab and the BSA may be immobilised on their respective beads by passive absorption or covalent linkage by methods known in the art. The beads are such that they may be moved along or through the membrane 2 as a result of the aforementioned liquid flow. The beads of the two sets may be of the same colour although for preference will be of different colours.

The sponge 3 further incorporates appropriate buffer (e.g. phosphate buffered saline).

More detailed consideration will now be given to each of regions 5–7.

Provided at region 5 (the threshold region) is an antigen Ag which will interact with antibody Ab inmmobilised on the latex beads. At region 6 (the detection region) there is immobilised anti antibody. This anti antibody is capable of interacting with a complex formed between hapten H (if present) and antibody Ab provided on the beads.

Region 7 is a control region (the purpose of which will be described below) and includes an antibody (e.g. Sheep anti BSA) which will interact with the BSA provided on the latex beads.

The antigen, anti antibody and antibody provided respectively at regions 5, 6 and 7 are immobilised on the membrane, e.g. by passive absorption or covalent attachment.

The use of the device will now be described.

A sample (e.g. 50–200 ml) of the liquid to be analysed is applied to the sponge 3 and causes the beads to migrate along the membrane in the direction of arrow 4.

If hapten H is present in the sample then it will interact with antibody Ab provided on the beads during the time scale of movement of the beads from sponge 3 to region 5.

Assuming that the hapten H is present in an amount above a certain critical concentration, a detectable quantity of beads will pass through region 5 and move forward to region 6.

At this region the beads having the antibody/hapten (Ab/H) conjugate are inmmobilised by the anti antibody and form a coloured band. Formation of this coloured region (the colour being provided by the beads) indicates a positive test.

The only beads which move forward from region 6 are those having immobilised BSA which interacts at control region 7 with the antibody to BSA. This results in a further coloured band being formed at region 7, the purpose of which is to indicate that the device is functioning correctly.

Considering now the case where the liquid sample does not contain hapten (or only contains hapten below a critical amount), the beads migrate as described above but are retained in region 5 thus forming a coloured band at that region. No band is formed at 6 although, as for a positive test, a band is formed at region 7.

Therefore, a positive test shows bands at regions 6 and 7 whereas a negative test shows bands at regions 5 and 7. If desired, region 5 may be obscured from view (e.g. by a cover 8 as represented by the dashed lines) so that a positive test is determined easily by the presence or absence of a band at region 6. The fact that a band appears at region 6 to indicate a positive test overcomes the disadvantage of the prior art that a positive test does not give rise to a coloured band (other than the control band).

I claim:

1. An analytical device for determining the presence of analyte species of interest in a liquid sample, the device comprising a chromatographic membrane support along which the liquid may travel, a plurality of first detectable particles associated with a sampling region of the device at which liquid is to be applied, said particles being capable of being moved along the support by said liquid travel and having immobilised thereon a first binding agent capable of forming a first complex with said analyte species, a threshold region provided downstream of the sampling region in the direction of liquid travel, said threshold region being provided with a second binding agent which is capable of binding to non-complexed first finding agent on the particles, and which is present in an amount, such that a detectable number of said particles only pass the threshold region if the amount of the analyte species in the sample is above a predetermined level, and a detection region downstream of said threshold region in the direction of liquid travel, said detection region comprising a third binding agent capable of binding to the first complex on the particles.

2. The device of claim 1 wherein the sampling region contains a set of second detectable particles which have immobilised thereon an immunological component which will not bind to the analyte species, the first binding agent, the second binding agent nor the third binding agent but which will bind to a complementary immunological component provided downstream of the detection region.

3. The device of claim 1 wherein the detection region comprises a plurality of bands of the third binding agent each of which allows a detectable quantity of particles to pass if the amount of analyte species is above a predetermined level.

4. The device of claim 1 for detecting an antibody.

5. The device of claim 4 wherein the first binding agent is an antigen to the analyte antibody, the second binding agent is an antibody, receptor or selective binding agent, and the third binding agent is an antibody to a complex formed between the analyte antibody and the first binding agent.

6. The device of claim 1 for detecting an antigen.

7. The device of claim 6 wherein the first binding agent is an antibody or selective binding agent for complexing with the analyte antigen, the second binding agent is an antigen capable of complexing with the first binding agent, and the third binding agent is an antibody to a complex formed between the analyte antigen and the first binding agent.

8. The device of claim 1 wherein the particles are of a contrasting color to the membrane support.

9. The device of claim 1 wherein the particles are fluorescent.

10. The device of claim 1 wherein the threshold region is obscured from view.

11. The device of claim 1 wherein the particles have a size in the range 1 to 5 microns.

12. The device of claim 1 wherein the particles are of latex.

13. The device of claim 1 wherein the support comprises a homogenous matrix.

14. The device of claim 1 wherein the support comprises nylon or nitrocellulose.

15. The device of claim 1 provided with a controlled release means to which the liquid sample is applied.

16. The device of claim 15 wherein the controlled release means is a filter pad or a sponge.

17. The device of claim 1 for detecting a hapten.

18. The device of claim 1 for detecting DNA.

19. The device of claim 1 for detecting RNA.

20. The device of claim 1 for detecting cells.

21. The device of claim 1 for detecting a virus.

* * * * *